(12) United States Patent
Strasemeier

(10) Patent No.: US 10,588,783 B2
(45) Date of Patent: Mar. 17, 2020

(54) METHOD AND APPARATUS FOR WEIGHTED RANDOM PATTERN PRINTING ON ABSORBENT ARTICLE COMPONENTS

(71) Applicant: The Procter & Gamble Company, Cincinnati, OH (US)

(72) Inventor: John Andrew Strasemeier, Aurora, IN (US)

(73) Assignee: The Procter & Gamble Company, Cincinnati, OH (US)

(*) Notice: Subject to any disclaimer, the term of this patent is extended or adjusted under 35 U.S.C. 154(b) by 102 days.

(21) Appl. No.: 15/872,183

(22) Filed: Jan. 16, 2018

(65) Prior Publication Data

US 2018/0200118 A1    Jul. 19, 2018

Related U.S. Application Data

(60) Provisional application No. 62/447,502, filed on Jan. 18, 2017.

(51) Int. Cl.
| | | |
|---|---|---|
| *A61F 13/15* | (2006.01) | |
| *B41J 3/407* | (2006.01) | |
| *B41J 11/00* | (2006.01) | |
| *A61F 13/84* | (2006.01) | |

(Continued)

(52) U.S. Cl.
CPC ........ *A61F 13/15585* (2013.01); *A61F 13/15* (2013.01); *A61F 13/15731* (2013.01); *A61F 13/51394* (2013.01); *A61F 13/51496* (2013.01); *A61F 13/84* (2013.01); *B41J 3/407* (2013.01); *B41J 3/4078* (2013.01); *B41J 11/002* (2013.01); *B41J 11/008* (2013.01); *A61F 2013/8497* (2013.01)

(58) Field of Classification Search
CPC . B41J 13/00; B41J 3/407; B41J 3/4078; B41J 11/008; B41J 11/002; A61F 13/15585; A61F 13/15; A61F 13/15731; A61F 13/51394; A61F 13/51496; A61F 13/84; A61F 2013/8497
See application file for complete search history.

(56) References Cited

U.S. PATENT DOCUMENTS

| | | |
|---|---|---|
| 2,075,189 A | 3/1937 | Galligan et al. |
| 3,025,199 A | 3/1962 | Harwood |
| 3,465,351 A | 9/1969 | Dahl et al. |

(Continued)

OTHER PUBLICATIONS

14607 PCT International Search Report and Written Opinion, dated Jun. 4, 2018 (4 pages).

*Primary Examiner* — Thinh H Nguyen
(74) *Attorney, Agent, or Firm* — C. Brant Cook

(57) ABSTRACT

Disclosed are methods and apparatuses for inkjet printing including printing graphics on an absorbent article component, comprising the steps of: providing one or more printheads; providing a substrate extending in a machine direction, the substrate comprising a first surface and an opposing second surface and defining a width in a cross direction; advancing the substrate in the machine direction past the one or more printheads; ejecting one or more inks from the one or more printheads onto the first surface of the substrate to define a graphic of a plurality of images, each of the plurality of images not being identical to another; wherein the distribution of each of the plurality of images printed on the substrate are not all equal to each other.

20 Claims, 11 Drawing Sheets

(51) Int. Cl.
*A61F 13/514* (2006.01)
*A61F 13/513* (2006.01)

(56) References Cited

U.S. PATENT DOCUMENTS

| | | |
|---|---|---|
| 3,848,594 A | 11/1974 | Buell |
| 3,860,003 A | 1/1975 | Buell |
| 4,107,364 A | 8/1978 | Sisson |
| 4,209,563 A | 6/1980 | Sisson |
| 4,515,595 A | 5/1985 | Kievit et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 5,151,092 A | 2/1992 | Buell et al. |
| 5,092,861 A | 3/1992 | Nomura et al. |
| 5,167,897 A | 12/1992 | Weber et al. |
| 5,221,274 A | 6/1993 | Buell et al. |
| 5,246,433 A | 9/1993 | Hasse et al. |
| 5,286,543 A | 2/1994 | Ungpiyakul et al. |
| 5,330,458 A | 7/1994 | Buell et al. |
| 5,359,525 A | 10/1994 | Weyenberg |
| 5,360,420 A | 11/1994 | Cook et al. |
| 5,562,646 A | 10/1996 | Goldman et al. |
| 5,569,234 A | 10/1996 | Buell et al. |
| 5,599,335 A | 2/1997 | Goldman et al. |
| 5,628,097 A | 5/1997 | Benson et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,897,545 A | 4/1999 | Kline et al. |
| 5,916,661 A | 6/1999 | Benson et al. |
| 5,928,212 A | 7/1999 | Kline et al. |
| 5,957,908 A | 9/1999 | Kline et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,251,097 B1 | 6/2001 | Kline et al. |
| 6,410,129 B2 | 6/2002 | Zhang et al. |
| 6,426,444 B2 | 7/2002 | Roe et al. |
| 6,432,098 B1 | 8/2002 | Kline et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,669,618 B2 | 12/2003 | Reising et al. |
| 6,790,798 B1 | 9/2004 | Suzuki et al. |
| 6,801,828 B2 | 10/2004 | Popp et al. |
| 6,820,022 B2 | 11/2004 | Popp et al. |
| 6,825,393 B2 | 11/2004 | Roe et al. |
| 6,861,571 B1 | 3/2005 | Roe et al. |
| 7,123,981 B2 | 10/2006 | Dollevoet et al. |
| 7,521,587 B2 | 4/2009 | Busam et al. |
| 7,923,597 B2 | 4/2011 | Ponomarenko et al. |
| 8,145,343 B2 | 3/2012 | DeBruler et al. |
| 8,145,344 B2 | 3/2012 | DeBruler et al. |
| 8,211,079 B2 | 7/2012 | Raycheck et al. |
| 8,244,393 B2 | 8/2012 | McLaughlin et al. |
| 8,273,066 B2 * | 9/2012 | Anderson ......... A61F 13/15203 604/385.01 |
| 9,139,747 B2 * | 9/2015 | Kamada ................ C09D 11/30 |
| 9,211,356 B2 | 12/2015 | Gruenbacher |
| 9,226,861 B2 | 1/2016 | LaVon et al. |
| 9,326,899 B2 | 5/2016 | Zink et al. |
| 2003/0233082 A1 | 12/2003 | Kline et al. |
| 2005/0217791 A1 | 10/2005 | Costello et al. |
| 2007/0093769 A1 | 4/2007 | Kline et al. |
| 2007/0239126 A1 | 10/2007 | Wilson et al. |
| 2008/0132872 A1 | 6/2008 | Trennepohl et al. |
| 2009/0312730 A1 | 12/2009 | LaVon et al. |
| 2011/0046591 A1 | 2/2011 | Warner |
| 2013/0211356 A1 | 8/2013 | Nishikawa et al. |

\* cited by examiner

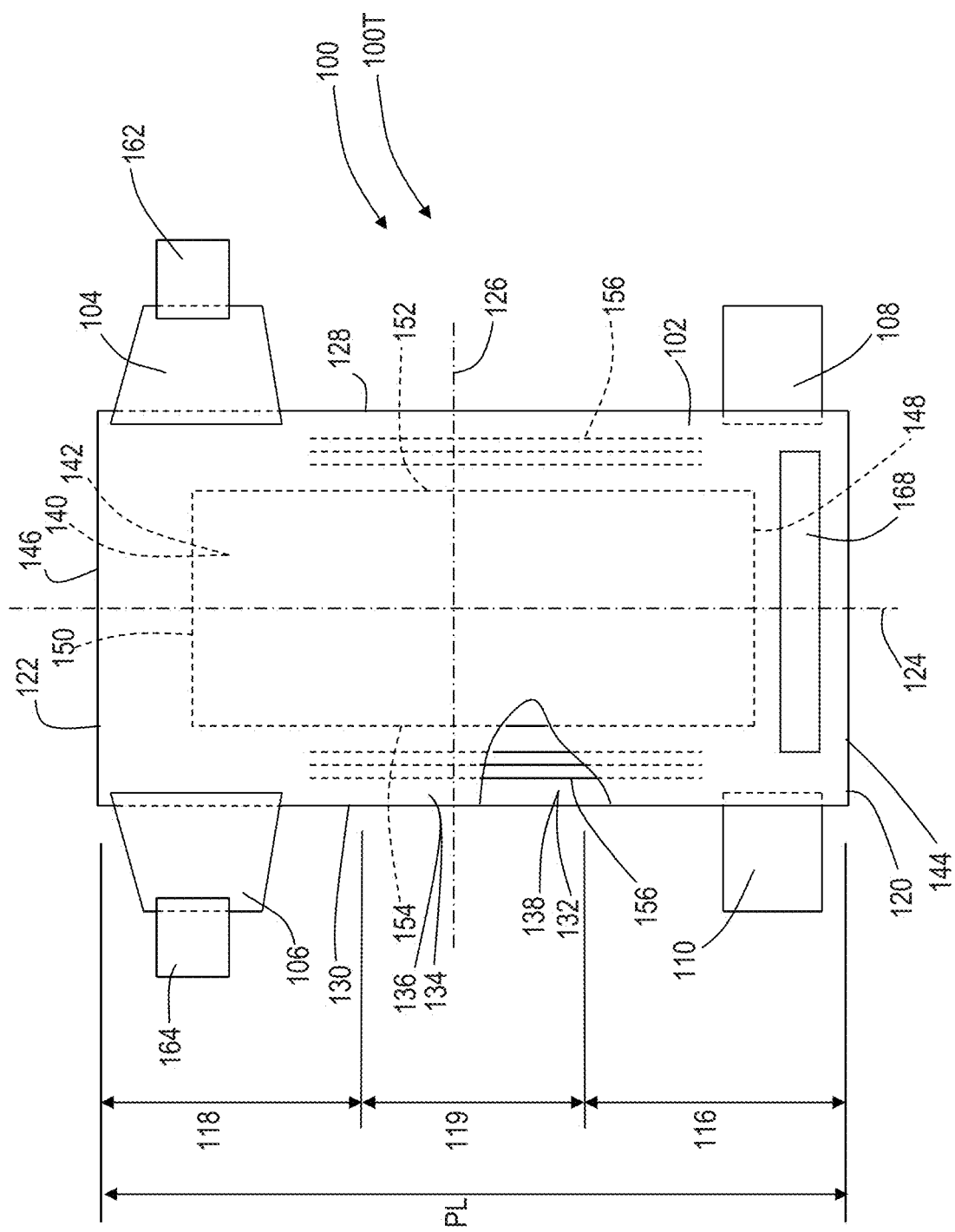

METHOD AND APPARATUS FOR WEIGHTED RANDOM PATTERN PRINTING ON ABSORBENT ARTICLE COMPONENTS

CROSS REFERENCE TO RELATED APPLICATION

This application claims the benefit of U.S. Provisional Application No. 62/447,502, filed Jan. 18, 2017, the substance of which is incorporated herein by reference.

FIELD OF THE INVENTION

The present disclosure relates to apparatuses and methods for inkjet printing absorbent article component substrates advancing in a machine direction, and more particularly, methods and apparatuses for printing particular distributions of different images on advancing substrates.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. In some configurations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like.

In some configurations, the printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. However, the above practice of separately printing the substrates offline from the converting lines typically requires additional cost associated with handling, winding and unwinding, storing and shipping of the substrates. In addition, the above steps can negatively affect the quality of the printed substrate, resulting in uneven and often excessive deformations of the wound layers of the substrate inside the roll due to uneven distribution of the compression forces inside the roll. Furthermore, the separately printed substrates often require special registration control methods to ensure proper phasing of the printed images with the converting operations to effect a desired and consistent positioning of the printed image in the produced article.

In an attempt to overcome the aforementioned drawbacks to offline printing, the graphic printing may be done online during the article assembly process. However, combining printing operations with converting operations may create other challenges in performing such printing processes when attempting to maintain aesthetically pleasing final assemblies. For example, contact printing processes, such as flexographic and rotogravure printing processes, may be capable of operating effectively on certain substrates at relatively high production rates. However, such contact printing processes have relatively low degrees of flexibility with regard to the ability to change the design of a printed graphic. When utilizing such contact printing methods, changes in graphic designs would often necessitate the shutdown and restart of the entire converting operation. In contrast, some types of printing processes, such as non-contact inkjet printing processes, may provide more flexibility and ease with regard to the ability to change the design of a printed graphic. In some configurations, a change in graphic design can be implemented by inputting commands to a programmed printhead controller to select a desired image to be printed. However, the use of such commands to periodically change a design may have limited abilities previously not recognized.

For example, it may be desirable to print particular distributions of different images that are not regularly periodic, which is to say, that such distributions would have a degree of randomness to them, and it may also be desirable to weight those distributions according to various factors, e.g. the cost of ink. It may be desirable to provide consumers with packages of absorbent articles having printed substrates bearing a variety of graphic patterns, randomly distributed in such packages. It may be desirable to manufacture absorbent articles having printed substrates bearing coupons or winning tickets a la Willy Wonka. It may be desirable to manufacture absorbent articles having printed substrates bearing a random distribution of graphic patterns: (a) weighted by the cost of ink used per graphic pattern, such that a target cost per manufacturing unit may be achieved; (b) weighted by the volume of ink usage of each color of ink being used, such that, e.g. the ink cartridges (or other reservoirs) of at least two colors are depleted at about or the same time, thus allowing for refilling to be coincident; and/or (c) weighted by drops fired for each printhead, such that, e.g. the useful lifetimes (based on drops fired) of at least two printheads may expire at about or the same time, thus allowing for replacement to be coincident.

It is believed that one or more of the methods and apparatuses for printing particular distributions of different images on advancing substrates disclosed herein may help address one or more of these desires.

SUMMARY OF THE INVENTION

The present disclosure relates to methods and apparatuses for inkjet printing including printing graphics on an absorbent article component, comprising the steps of: providing one or more printheads; providing a substrate extending in a machine direction, the substrate comprising a first surface and an opposing second surface and defining a width in a cross direction; advancing the substrate in the machine direction past the one or more printheads; ejecting one or more inks from the one or more printheads onto the first surface of the substrate to define a graphic of a plurality of images, each of the plurality of images not being identical to another; wherein the distribution of each of the plurality of images printed on the substrate are not all equal to each other.

BRIEF DESCRIPTION OF THE DRAWINGS

FIG. 1A is a partially cut away plan view of an absorbent article in the form of a taped diaper that may include one or more substrates printed in accordance with the present disclosure with the portion of the diaper that faces away from a wearer oriented towards the viewer.

DETAILED DESCRIPTION OF THE INVENTION

Figure 1B:
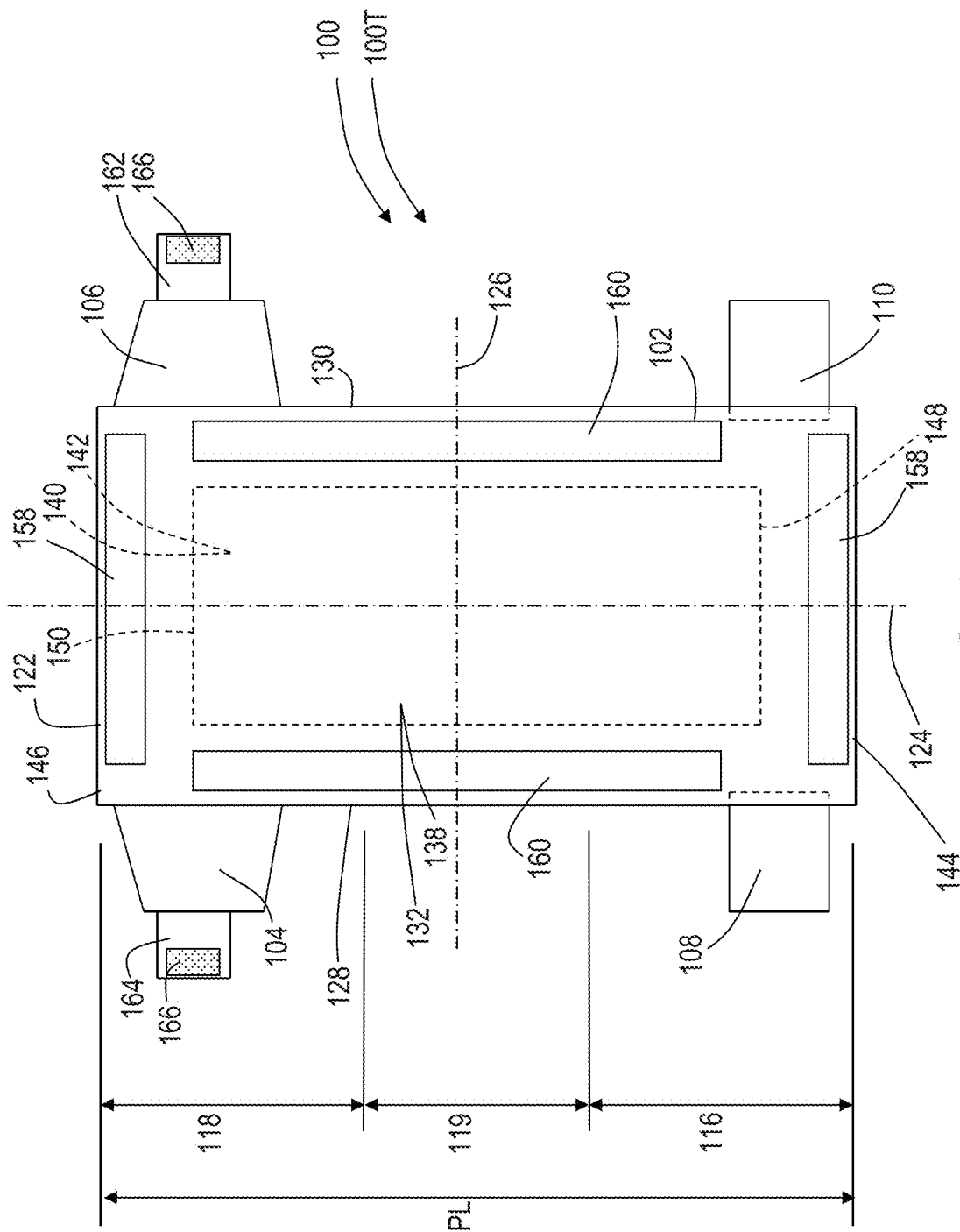
FIG. 1B is a plan view of the absorbent article of FIG. 1A that may include one or more substrates printed in accordance with the present disclosure with the portion of the diaper that faces toward a wearer oriented towards the viewer.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner). Non-limiting examples of absorbent articles include baby diapers, infant training pants, adult incontinence products, and feminine hygiene sanitary pads and pantiliners.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. ⅟₁₀ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

The term "print resolution" as used herein is defined in terms of inkjet printing technology by Dots Per Inch (dpi), wherein dpi defines a density of dots of ink that can be printed across a one inch length of a substrate. It is to be appreciated that the printheads herein may be configured to print at various print resolutions in the cross direction CD and the machine direction MD.

The present disclosure relates to methods and apparatuses for inkjet printing absorbent article substrates, and in particular, methods and apparatuses for printing particular distributions of different images on advancing substrates. More specifically, the methods and apparatuses herein include inkjet printing including printing graphics on an absorbent article component, comprising the steps of: providing one or more printheads; providing a substrate extending in a machine direction, the substrate comprising a first surface and an opposing second surface and defining a width in a cross direction; advancing the substrate in the machine direction past the one or more printheads; ejecting one or more inks from the one or more printheads onto the first surface of the substrate to define a graphic of a plurality of images, each of the plurality of images not being identical to another; wherein the distribution of each of the plurality of images printed on the substrate are not all equal to each other.

It is to be appreciated that the systems and methods disclosed herein are applicable to work with various types of converting processes and/or machines, such as for example, absorbent article manufacturing, packaging, and/or printing processes. The methods and apparatuses are discussed below in the context of manufacturing diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes a chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least 60%, 70%, 80%, 85%, 90%, 95%, or even 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "prestrained" or "mechanically prestrained" (subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107, 364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 and 2007/0093769.

Figure 1C:
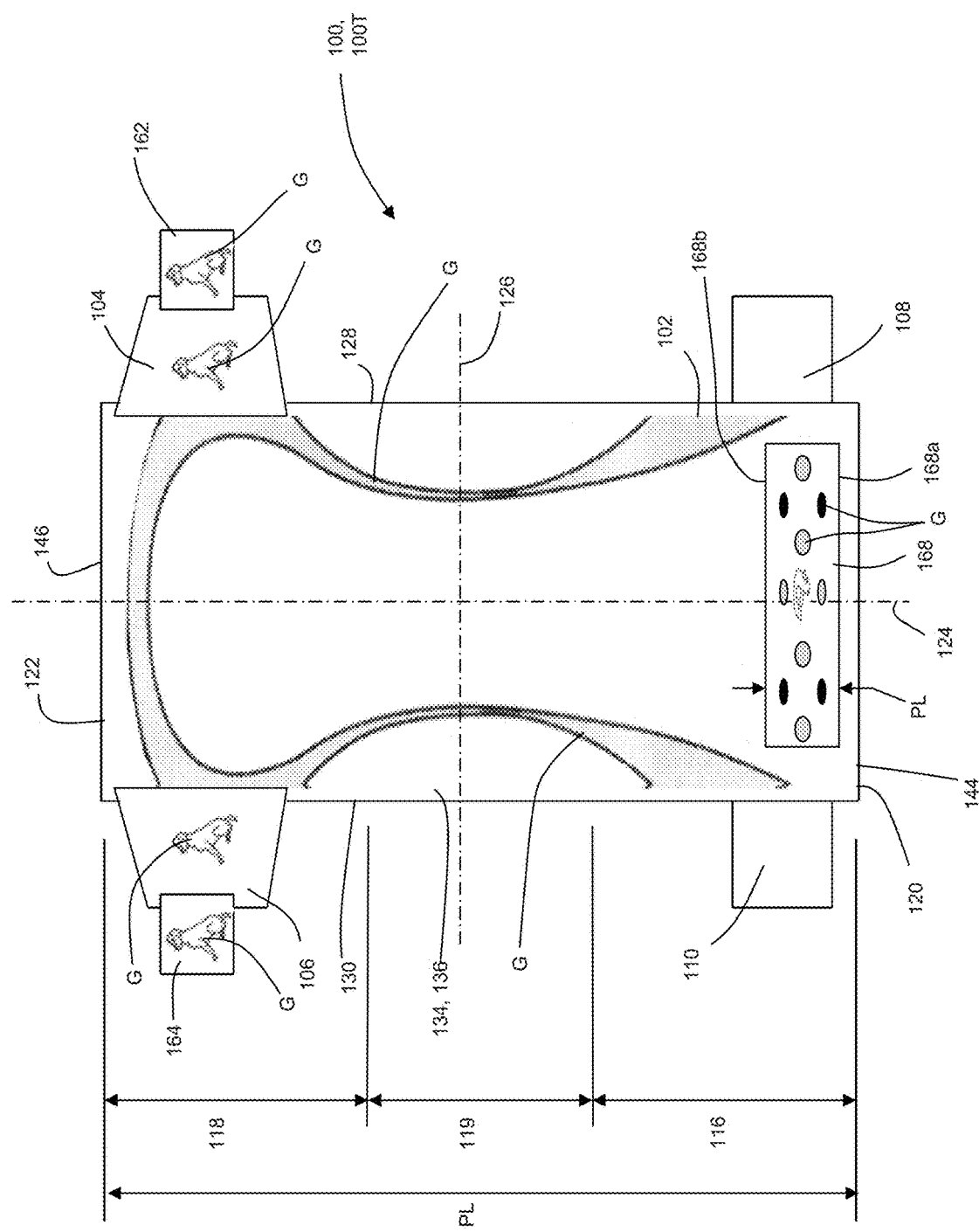
FIG. 1C is a plan view of a diaper with graphics on a backsheet and a connection zone.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper, such as shown in FIG. 1C. As such, the connection zone 168 may have a pitch length PL defined by a distance extending between a first lateral end edge 168a and the second lateral end edge 168b. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2A:
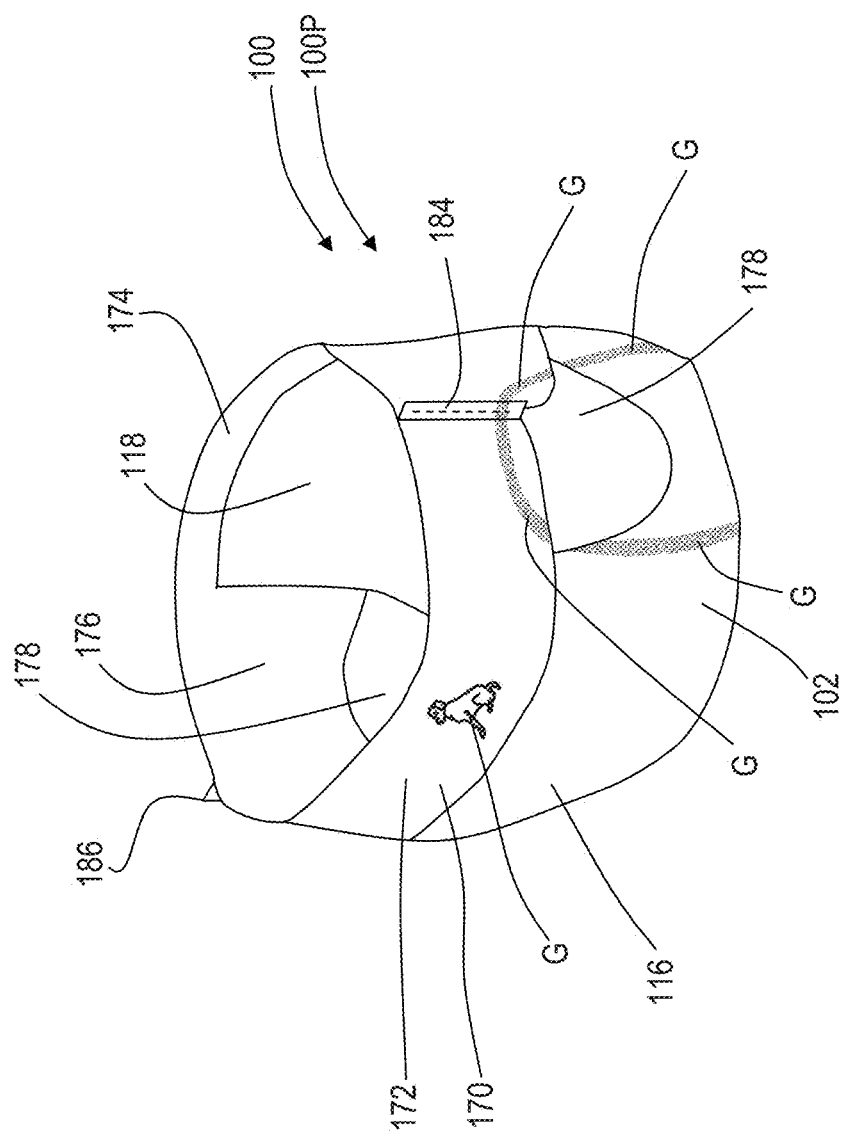
FIG. 2A is a front perspective view of an absorbent article in the form of a diaper pant with graphics on a chassis and front and rear belts.
Figure 2B:
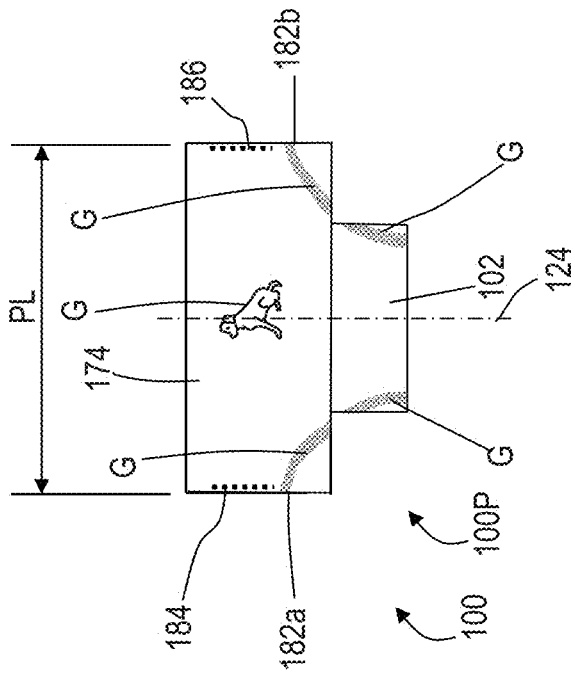
FIG. 2B is a front view of the absorbent article of FIG. 2A.
Figure 2C:
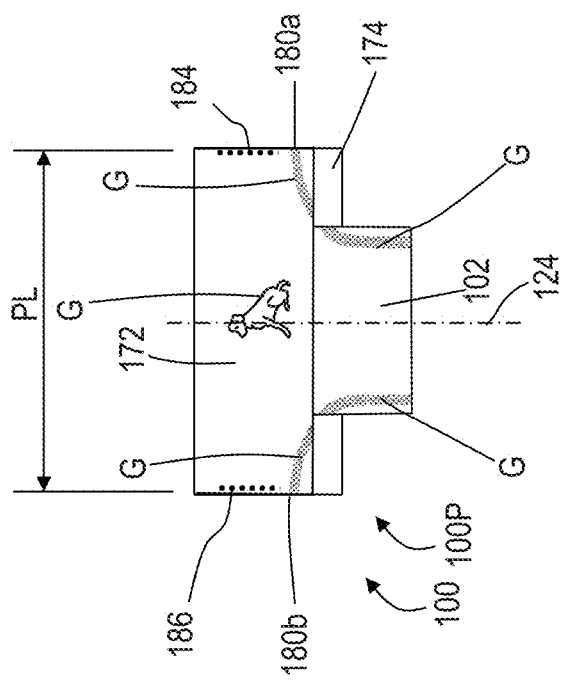
FIG. 2C is a rear view of the absorbent article of FIG. 2A.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PL, of the first elastic belt 172, and the distance between the first longitudinal side edge 182a and the second longitudinal side edge 182b defines the pitch length, PL, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various components that may be printed off-line, before assembly, or on-line, as part of the assembly process. As such, the absorbent articles herein may include graphics printed on various components. Thus, in the context of the previous discussion, the apparatuses and methods herein may be used to print substrates configured as continuous substrates and/or discrete components of an absorbent article 100, either off-line or on-line. For example, the apparatuses and methods herein may be utilized in to print graphics on any of the topsheet 138; backsheet 136; absorbent core 140; leg cuffs 156; waist feature 158; side panels 104, 106, 108, 110; connection zones 168; fastening elements 162, 166, and/or belts before, during, and/or after the manufacture of an absorbent article 100. For example, the backsheet 136 of the taped diaper 100T shown in FIG. 1C includes graphics G that may be printed before, during, and/or after assembly. The connection zone 168 shown in FIG. 1C may also include graphics G printed before, during, and/or after assembly. In yet another example, the front belt 172 and rear belt 174 of the diaper pant 100P may include graphics G printed before, during, and/or after assembly. As discussed in more detail below, the systems and methods herein may be utilized print such graphics during before or during assembly.

Figure 3:
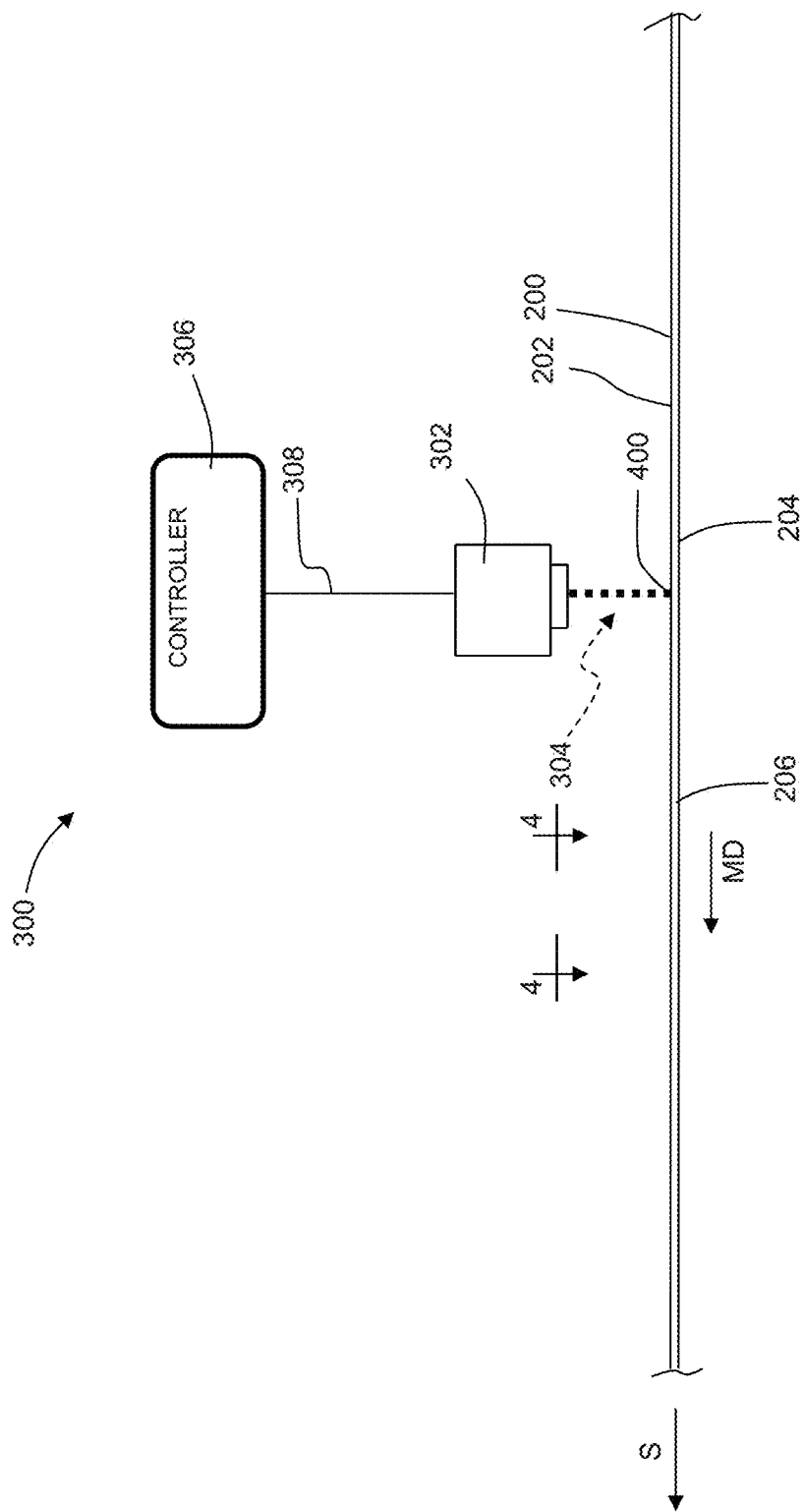
FIG. 3 is a schematic side view of a printing system for printing an advancing substrate.

It is to be appreciated that the printing systems and methods disclosed herein are applicable to work with various types of converting processes and/or machines. For example, FIG. 3 shows a schematic representation of a converting process including an inkjet apparatus or system 300 for printing graphics on a substrate 200 advancing in a machine direction MD. The substrate 200 may be a continuous substrate and may include a first surface 202 and an opposing second surface 204. The substrate 200 may also define a width W extending in the cross direction CD between a first longitudinal side edge 206 and a second longitudinal side edge 208.

Figure 4:
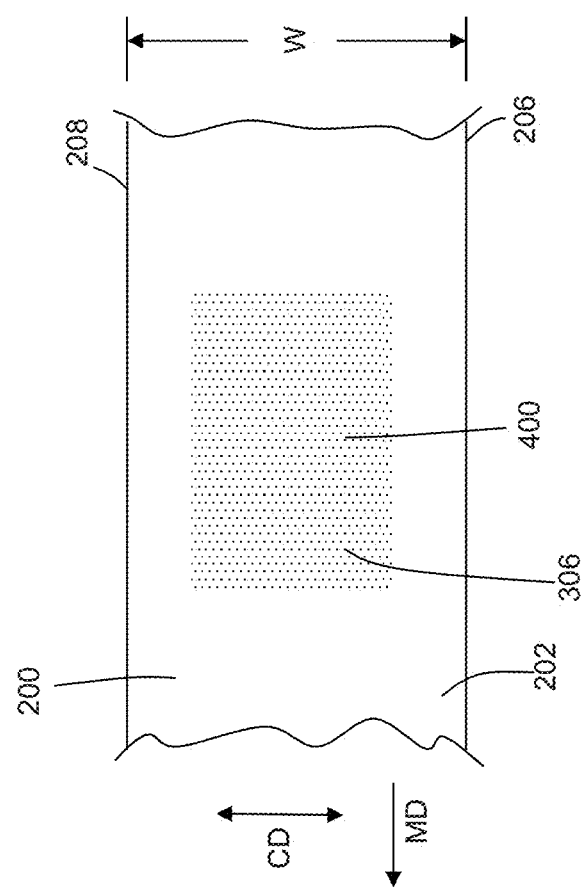
FIG. 4 is a top side view of the advancing substrate taken along the sectional line 4-4 of FIG. 3.
Figure 5A:
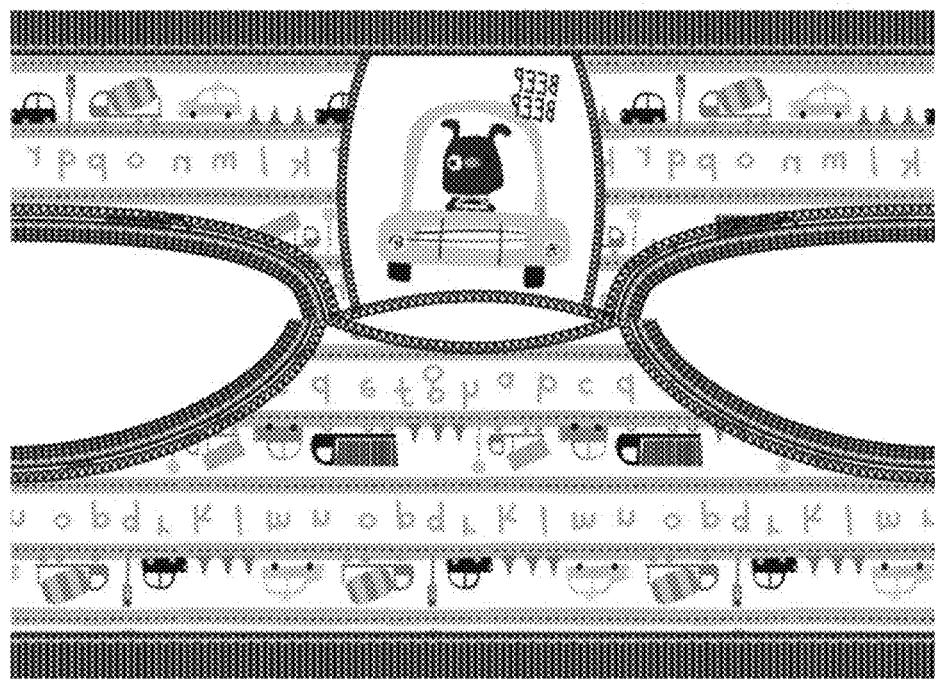
FIG. 5A is a top side view of an absorbent article component with graphics on front and back waist regions.
Figure 5B:
FIG. 5B is a top side view of an absorbent article component with graphics on front and back waist regions.
Figure 5C:
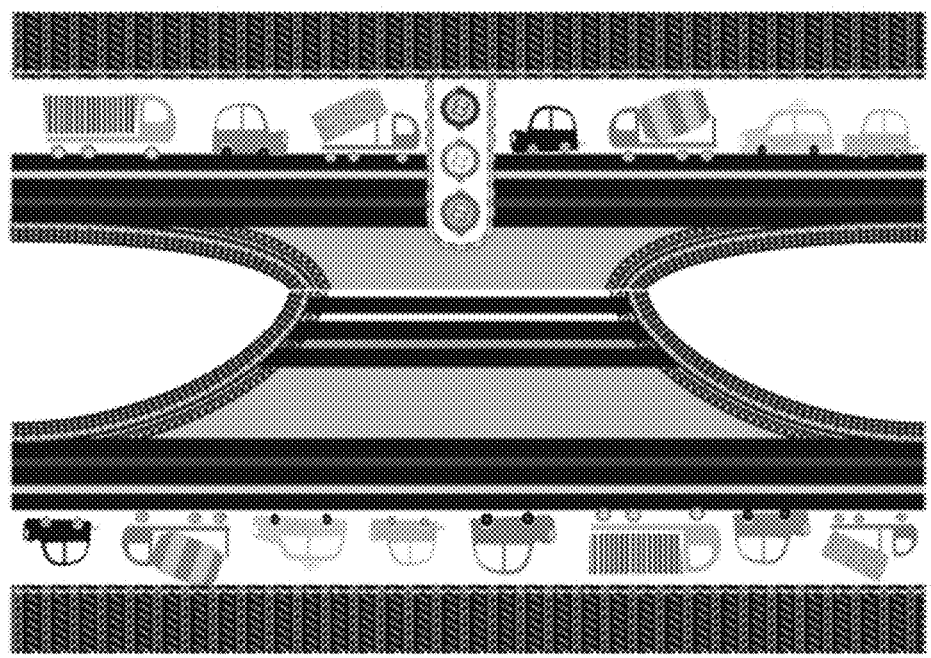
FIG. 5C is a top side view of an absorbent article component with graphics on front and back waist regions.
Figure 5D:
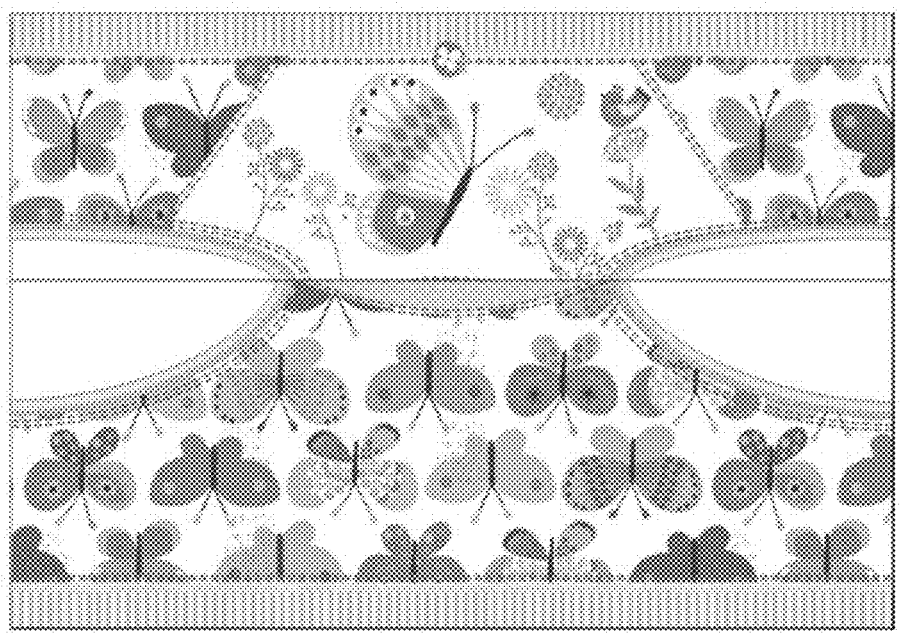
FIG. 5D is a top side view of an absorbent article component with graphics on front and back waist regions.
Figure 5E:
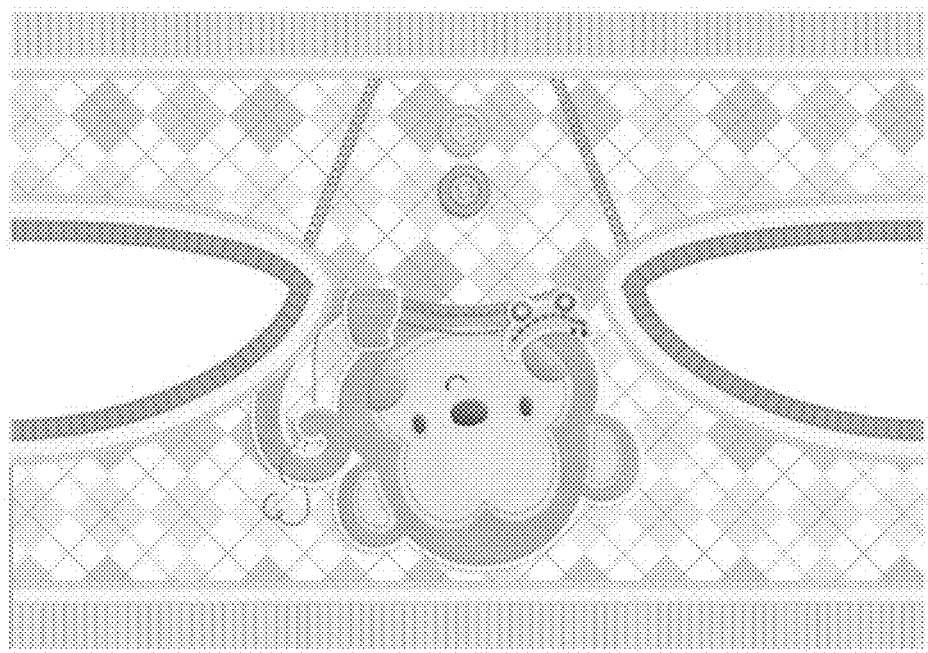
FIG. 5E is a top side view of an absorbent article component with graphics on front and back waist regions.
Figure 5F:
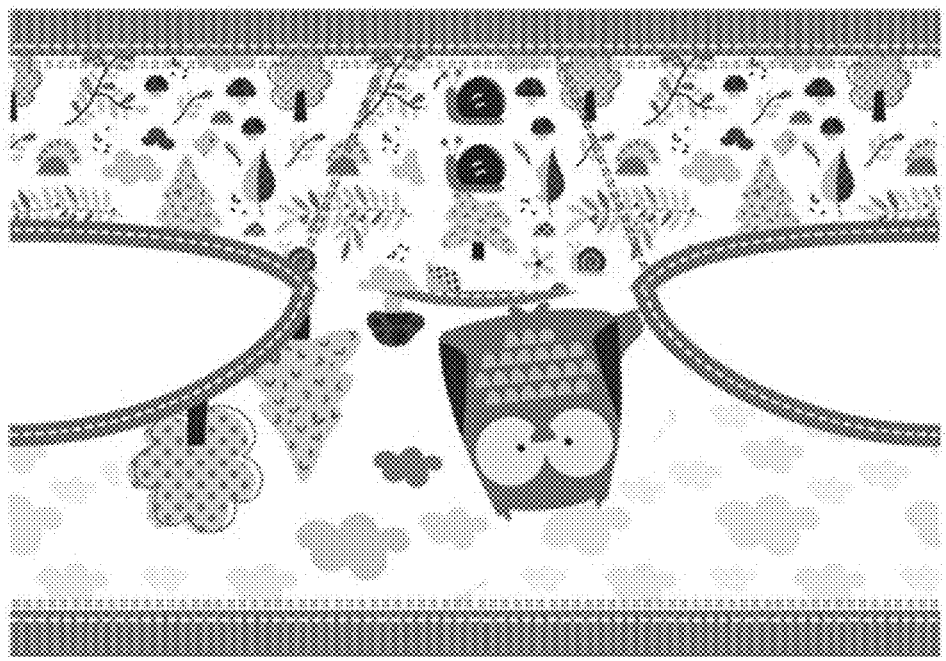
FIG. 5F is a top side view of an absorbent article component with graphics on front and back waist regions.
Figure 5G:
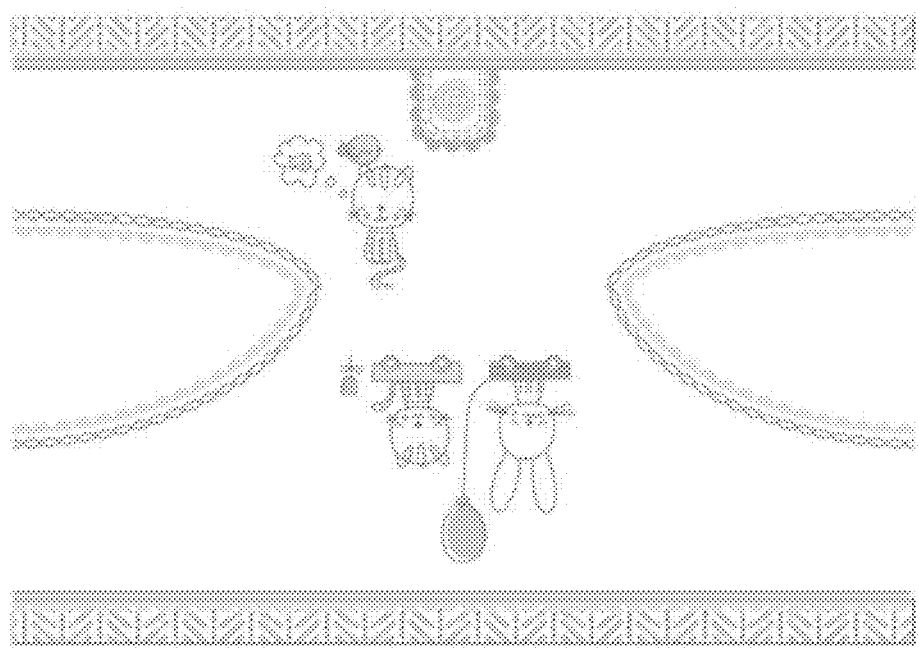
FIG. 5G is a top side view of an absorbent article component with graphics on front and back waist regions.

As shown in FIG. 3, the printing system 300 may include one or more printheads 302. During operation, the substrate 200 advances in the machine direction MD under the printhead 302. As shown in FIGS. 3 and 4, the printhead ejects ink 304 onto the first surface 202 of the advancing substrate 200 to define a printed region 400 on the first surface 202, wherein the printed region 400 is printed at a desired print resolution. It is to be appreciated that the advancing substrate 200 may be supported in various ways to mitigate movement toward and away from the printhead 302. For example, the second surface 204 of the substrate 200 may be supported by a conveyor having a series of rollers, an advancing belt, and/or a rotating drum. It is to be appreciated that the substrate 200 may be subject to additional manufacturing operations, such as combining and/or cutting operations, during assembly of a product.

The printing systems 300 may create printed regions 400 when printing on substrates 200 having relatively rough first surfaces 202, such as a nonwoven. Thus, it is to be appreciated that the substrate 200 herein may be configured as single nonwoven substrate that defines both the first surface 202 and the second surface 204. It is also to be appreciated that the substrate 200 herein may be configured as a laminate including various layers of substrates bonded together, wherein a nonwoven substrate layer defines the first surface 202 and another substrate layer defines the second surface 204. For example, the substrate 200 may include a nonwoven substrate layer that defines the first surface 202 and a second substrate layer defining the second surface 204, wherein the second substrate layer may include a nonwoven or a film.

With continued reference to FIG. 3, it is to be appreciated that the printing apparatus 300 herein may include various quantities of non-contact printheads 302 arranged and/or configured in various ways to deposit inks onto the advancing substrate 200 to create printed regions 400. For example, in some embodiments, the printheads herein may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, "drop-on-demand" and "continuous" inkjet printing.

With "continuous" inkjet printing processes, an ink is supplied under pressure to an inkjet nozzle and forced out through a small orifice. Prior to passing out of the nozzle, the pressurized ink stream proceeds through a ceramic crystal which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

As previously mentioned, the printing system 300 herein may be configured with various quantities and types of printheads that operate to deposit inks on an advancing substrate at various rates. And the printhead 302 shown in FIG. 3 may be configured as an inkjet printhead. As such, when the printhead 302 fires, a drop of ink 304 is discharged from an orifice in the printhead 302. The rate at which drops of ink are discharged from an orifice in a printhead is referred to herein as "firing frequency" and may be expressed in units of kilohertz (kHz). In turn, the printheads herein may be configured to operate at various firing frequencies at or below a maximum firing frequency of the printhead. As such, it is to be appreciated that the printing system 300 herein may be configured with various quantities of printheads that may be configured to operate at the same or different firing frequencies. In addition, the printheads herein may be configured with the same or different maximum firing frequencies. For example, in some configurations, the printheads herein may be configured with maximum firing frequencies that are equal to or greater than 5 kHz, and may be configured with maximum firing frequencies of about 5 kHz to about 120 kHz, specifically reciting all 0.1 kHz increments within the above-recited ranges and all ranges formed therein or thereby. In some embodiments, the printheads herein may be configured with maximum firing frequencies of equal to or less than about 20 kHz or about 30 kHz.

It is also to be appreciated that the printing system 300 herein may be configured to operate with various types of inks or ink systems, such as solvent-based, water-based, and ultraviolet (UV) cured inks. An "ink" is a liquid containing coloring matter, for imparting a particular hue to a substrate. An ink may include dyes, pigments, organic pigments, inorganic pigments, and/or combinations thereof. A non-limiting example of an ink would encompass spot colors. Additional non-limiting examples of inks include inks having white color. Additional non-limiting examples of inks include hot melt inks.

Some primary differences among the ink systems may relate to the method used for drying or curing the ink. For example, solvent-based and water-based inks are dried by evaporation, while UV cured inks are cured by chemical reactions. Inks may also include components, such as solvents, colorants, resins, additives, and (for ultraviolet inks only) UV-curing compounds, that are responsible for various functions. In some embodiments, a multi-stage printing system may be utilized. In some embodiments, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis. Some embodiments may utilize inks such as Artistri® Inks available from DuPont™, including 500 Series Acid Dye Ink; 5000 Series Pigment Ink; 700 Series Acid Dye Ink; 700 Series Disperse Dye Ink; 700 Series Reactive Dye Ink; 700 Series Pigment Ink; 2500 Series Acid Dye Ink; 2500 Series Disperse Dye Ink; 2500 Series Reactive Dye Ink; 2500 Series Pigment Dye Ink; 3500 Series Disperse Dye Ink; 3500 Series Pigment Dye Ink; and Solar Brite™ Ink. Ink such as disclosed in U.S. Pat. No. 8,137,721 may also be utilized. Water-based inks that may be utilized are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green). Some embodiments may utilized water based inks composed of food-grade ingredients and formulated to be printed directly onto ingestible food or drug products, such as Candymark Series inks available in colors such as black pro, red pro, blue pro, and yellow pro, available from Inkcups located in Danvers, Mass. Other broad ranges of general purpose and specialty inks may also be used, including food grade inks available from Videojet Technologies Inc. located in Wood Dale, Ill. Additional example inks include Collins 186-150-6 LED Cyan Ink; Collins 186-150-7 LED Magenta Ink; Collins 186-150-6 LED Yellow Ink; Collins 186-150-5 LED Black Ink; and Videojet Ink 99-51SR.

With continued reference to FIG. 3, it is to be appreciated that the printing apparatus 300 herein may be configured in various ways and may include various types of printing accessories. In some configurations, the printing apparatus 300 may include a corona treater, which may be positioned upstream of the printhead 302. The corona treater may be configured to increase the surface energy of the surface of the substrate 200 to be printed. In some embodiments, the corona treater may be configured to increase the surface energy of the surface to be printed to about 42 dynes/cm. In some configurations, the printing apparatus 300 may print energy curable ink, such as ultraviolet or electron beam curable inks, and thus, may also include an ink curing apparatus. In some configurations, the ink curing apparatus may be in the form of an ultraviolet (UV) light source that may include one or more ultraviolet (UV) lamps, which may be positioned downstream of the printhead 302 to help cure inks deposited onto the substrate 200. In some configurations, the ink curing apparatus may also include an infrared (IR) dryer light source that may include one or more infrared (IR) lamps, which may be positioned downstream of the printhead 302 to help dry water-based or solvent-based inks deposited onto the substrate 200 to form the graphics. In some configurations, the ink curing apparatus may include an electron beam (EB or e-beam) generator that may include one or more e-beam electrodes, which may be positioned downstream of the printhead 302 to help cure inks deposited onto the substrate 200.

As previously mentioned, the printing system 300 may be configured to print off-line or interact with and/or be configured as a unit operation of a converting line. In some configurations of the printing system 300, the printhead 302 may be arranged adjacent the advancing substrate 200, and the printhead 302 may interface and communicate with a controller 306. The controller 306 may be adapted to control the operation of the printheads and/or allow an operator to manually program the type of graphics to be printed. For example, the printing system 300 may be configured with various features, such as available on the XD070 Multi-Color Industrial Ink Jet unit available from Pad Print Machinery of Vermont. In some configurations, the printing system 300 may be configured to interface with other computerized systems and/or networks that may automatically program or command the printing system to print various graphics based on various input, such as sales orders from customers. It is to be appreciated that the controller 306 may be configured in various ways. For example, the controller 306 may be in the form of a personal computer (PC) or a central processing unit (CPU). The controller 306 may also be configured to monitor and affect various operations on a converting line. For example, the controller 306 may send various types of control commands to the converting line based on communications with sensors adjacent the converting line.

It is to be appreciated that the controller 310 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the controller 310 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIG. 3, the printhead 302 may be in communication with the controller 306 through a communication network 308. As such, it is to be appreciated that the controller 306 may be physically located near the advancing substrate 200 and/or printhead 302 and/or may be located at another location and in communication with the printhead 302 via a wired and/or wireless network 308. In some embodiments, the communication network 308 is configured as a non-deterministic communication network, such as for example, Ethernet or Ethernet IP (industrial protocol) communication network.

Referring again to FIGS. 3 and 4, during operation, the substrate 200 advances at a speed S in the machine direction MD under the printhead 302. The printhead 302 ejects the ink 304 onto the first surface 202 of the advancing substrate 200 to define the printed region 400 on the first surface 202. The printed region is generically represented in FIG. 4 as a rectangular shape on the first surface 202 of the substrate 200. Although a single printed region 400 is shown in FIG. 4, it is to be appreciated that the printhead 302 can be configured to print a plurality of printed regions arranged along the machine direction MD and/or cross direction of the substrate 200. It is to be appreciated that a single printed region 400 or a plurality of printed regions 400 may form a graphic.

It is to be appreciated that the printing systems 300 herein may be configured to print printed regions 400 at desired print resolutions on a substrate 200, wherein the printed regions may form graphics G, such as discussed above with reference to absorbent articles assembled with various components that may be printed off-line, before assembly, or on-line, as part of the assembly process. Thus, in the context of the previous discussion, the printing system 300 herein may be used to print substrates and components of an absorbent article 100, either off-line or on-line. For example, the printing system 300 herein may be utilized to print printed regions to form graphics on any of the topsheet 138; backsheet 136; absorbent core 140; leg cuffs 156; waist feature 158; side panels 104, 106, 108, 110; connection zones 168; fastening elements 162, 166, and/or belts before or during the manufacture of an absorbent article 100.

Although the above discussion often refers to figures illustrating a printing system having a single printhead 302, it is to be appreciated that the printing systems herein may be configured with more than more than one printhead arranged in the cross direction CD and/or machine direction MD. In some configurations, the print system 300 herein may include backup printheads, such as disclosed in U.S. Pat. No. 6,811,239. It is also to be appreciated that the printheads may be configured to print inks having the same colors or different colors. For example, a first ink may comprise a first color, and a second ink may comprise a second color different from the first color. In another example, a first ink may comprise a first color, and a second ink may comprise a second color that is the same as the first color. In addition, the printheads herein may be configured to perform single color, multi-color, half tone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "case color," as used herein, refers to a color that is used in the halftoning printing process as the foundation for creating additional colors. In some non-limiting embodiments, a base color is provided by a colored ink. Non-limiting examples of base colors may selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least three of the primary of colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

The present method provides for printing particular distributions of different images on advancing substrates. For a given set of images, certain characteristics of the images and the components of the image are determined. The length of the image, the width of the image, and the number of pixels in each color plane (e.g. cyan, magenta, yellow, and black) needed to create each image, are measured or calculated. The MD printer resolution, CD printer resolution, and ink drop volume, along with the aforementioned image details are used to calculate the amount of ink needed to print each image. The cost of the ink per unit volume is used to calculate the ink cost associated with each image. An example is shown below.

| Image No. | Image Length (mm) | Image Width (mm) | Total Ink Pixels | Ink Drop Volume (pL) | Total Ink Usage (mL) | Ink Cost ($/L) | Image Ink Cost per 1000 Pieces ($) |
|---|---|---|---|---|---|---|---|
| 1 | 1000 | 1000 | 24800050 | 1 | 0.024800050 | 100 | 2.48 |
| 2 | 1000 | 1000 | 49600099 | 1 | 0.049600099 | 100 | 4.96 |
| 3 | 1000 | 1000 | 74400149 | 1 | 0.074400149 | 100 | 7.44 |
| 4 | 1000 | 1000 | 99200198 | 1 | 0.099200198 | 100 | 9.92 |

Using conventional printing methods, the four images are printed sequentially and repetitively, i.e. 1, 2, 3, 4, 1, 2, 3, 4, 1, 2 . . . and so on, and as such, each image is equally printed. For four images, each image is printed 25% of the time, and the average cost to print the images for a given quantity, e.g. 1000 images, is the average cost of the four images, as shown below.

| Image No. | Probability (%) | Image Ink Cost per 1000 Pieces ($) |
|---|---|---|
| 1 | 25 | 2.48 |
| 2 | 25 | 4.96 |
| 3 | 25 | 7.44 |
| 4 | 25 | 9.92 |

$$\text{Average Cost per 1000 pieces} = \frac{\$2.48 + \$4.96 + \$7.44 + \$9.92}{4} = \$6.20$$

Using the printing methods herein which provide for weighted probability printing, each of the four images need not be equally printed, albeit the total probability of the four images being printed must equal 100%. The skilled person may select from many different combinations of probabilities for each image, provided that the sum of the probabilities is 100%, wherein the average cost to print the images for a given quantity, e.g. 1000 images, is the based on the proportional cost of each of the four images, as shown below.

| Image No. | Probability (%) | Image Ink Cost per 1000 Pieces ($) |
|---|---|---|
| 1 | 50 | 2.48 |
| 2 | 25 | 4.96 |
| 3 | 13 | 7.44 |
| 4 | 12 | 9.92 |

Average Cost per 1000 pieces=50%×$2.48+25%×$4.96+13%×$7.44+12%×$9.92=$4.64

As shown above, the average cost of printing 1000 pieces (absorbent articles or components thereof) may be reduced from $6.20 using conventional printing methods to $4.64, using the methods herein, assuming all other factors are held constant.

Using the printing methods herein which provide for weighted probability printing, instructions for printing certain images in desired distributions may be provided to the printing apparatus, e.g. a printing system 300, via, e.g. a controller 306. Each image may be loaded to the printing system and assigned a unique number corresponding to that image. Image 1 will be printed when the number one is presented to the printer, Image 2 will be printed when the number two is presented to the printer, and so on. A list of the unique numbers and a random distribution of those numbers according to the desired probability may be prepared. A suitable method of preparing this is to create a "csv" (comma-separated value) file using, e.g. Microsoft Excel, with each unique number listed in a first column. A random distribution of those unique numbers may be generated, by the program, in all rows of the first column of the csv file, based on the probability indicated/desired. The printing system may be instructed to print the image corresponding to the unique number in the order and in the distribution generated. If desired, the number of rows in in the random distribution may be selected to modify the length of the repeating loop of printing. For example, for 3 images, numbered 1, 2, and 3, and a distribution of 50% Image 1, 30% Image 2, and 20% Image 3, a random distribution of 10 rows may yield: 1, 1, 2, 1, 2, 1, 3, 2, 1, 3; while a random distribution of 20 rows of the same distribution and same images may yield: 3, 1, 2, 1, 2, 1, 3, 2, 1, 2, 2, 1, 1, 1, 2, 1, 1, 3, 1, 3.

Example

The following example may be useful in understanding the present disclosure. The absorbent article components with graphics depicted in FIGS. 5A to 5G are assigned corresponding unique image numbers 1 to 7, i.e. FIG. 5A=Image 1, FIG. 5B=Image 2, and so on, and the following characteristics of the images and components of the images, the printer, and the inks, are assumed:
MD Resolution=400 dpi
CD Resolution=400 dpi
Drop Volume=10 pL
MD Image Length=500 mm
CD Image Length=300 mm
Ink Cost=$100/L Using these assumptions, ink coverage (%) and total pixels may be determined, as shown below, for Image 1. A suitable method of determining ink coverage, which in turn, may be used to determine total pixels, is to use a photo editing computer program containing a histogram feature, e.g. using Adobe Photoshop and obtaining the mean value for a given color using Photoshop's histogram feature, where the Channel Mean value ranges from 0 to 255, depending on the color intensity at each level of the image, as indicated by the program.

| Color Plane | MD Resolution (dpi) | CD Resolution (dpi) | MD Length (mm) | CD Length (mm) | Channel Mean | Ink Coverage (%) | Pixels |
|---|---|---|---|---|---|---|---|
| Cyan | 400 | 400 | 500 | 300 | 196.3 | 23.0 | 8,564,770 |
| Magenta | 400 | 400 | 500 | 300 | 227.9 | 10.6 | 3,954,878 |
| Yellow | 400 | 400 | 500 | 300 | 236.1 | 7.4 | 2,761,558 |
| Black | 400 | 400 | 500 | 300 | 226.3 | 11.3 | 4,188,291 |
| | | | | | TOTAL | 52.3 | 19,469,498 |

Color 1 Pixel Count =

$$MDRes \times CDRes \times MDLength \times CDLength \times Color1\%Coverage$$

$$Color1\%Coverage = \frac{255 - Mean}{255}$$

Total Pixel Count =

$$Color1PixelCount + Color2PixelCount + \cdots + ColorNPixelCount$$

The total pixel count for each image, the ink drop volume, and the bulk ink cost are used to calculate the ink cost per manufacture quantity, here 1000 images, as shown below.

| Image No. | Total Pixels | Ink Drop Volume (pL) | Ink Usage (mL) | Ink Cost ($/L) | Image Ink Cost per 1000 Pieces ($) |
|---|---|---|---|---|---|
| 1 | 19,469,498 | 10.0 | 0.195 | 100.00 | 19.47 |
| 2 | 4,259,409 | 10.0 | 0.043 | 100.00 | 4.26 |
| 3 | 38,955,918 | 10.0 | 0.390 | 100.00 | 38.96 |
| 4 | 14,805,630 | 10.0 | 0.148 | 100.00 | 14.81 |
| 5 | 7,387,935 | 10.0 | 0.074 | 100.00 | 7.39 |
| 6 | 17,896,965 | 10.0 | 0.179 | 100.00 | 17.90 |
| 7 | 2,790,006 | 10.0 | 0.028 | 100.00 | 2.79 |

Ink Usage (mL)=Total Pixels×Ink Drop Volume

Ink Cost per 1000 prints($)=Ink Usage×Ink Cost× 1000

Using conventional printing methods, the seven images are printed sequentially and repetitively, i.e. 1, 2, 3, 4, 5, 6, 7, 1, 2, 3, 4, 5, 6, 7, 1, 2 . . . and so on, and as such, each image is equally printed. For seven images, each image is printed about 14.29% of the time, and the average cost to print the images for a given quantity, e.g. 1000 images, is the average cost of the seven images, as shown below.

Average Cost per 1000 pieces =

$$\frac{\$19.47 + \$4.26 + \$38.96 + \$14.81 + \$7.39 + \$17.90 + \$2.79}{7} = \$15.08$$

Using the printing methods herein which provide for weighted probability printing, each of the seven images need not be equally printed, albeit the total probability of the seven images being printed must equal 100%. The skilled person may select from many different combinations of probabilities for each image, provided that the sum of the probabilities is 100%, wherein the average cost to print the images for a given quantity, e.g. 1000 images, is the based on the proportional cost of each of the seven images, as shown below.

| Image No. | Probability (%) | Image Ink Cost per 1000 Pieces ($) | Weighted Ink Cost per 1000 Pieces ($) |
|---|---|---|---|
| 1 | 6 | 19.47 | 1.17 |
| 2 | 22 | 4.26 | 0.94 |
| 3 | 5 | 38.96 | 1.95 |
| 4 | 5 | 14.81 | 0.74 |
| 5 | 21 | 7.39 | 1.55 |
| 6 | 10 | 17.90 | 1.79 |
| 7 | 31 | 2.79 | 0.86 |
| TOTAL | 100.0 | N/A | 9.00 |

Average Cost per 1000 pieces=Probability1×InkCost1+Probability2×InkCost2+ . . . +Probability$N$×InkCost$N$ As shown above, the average cost of printing 1000 pieces (absorbent articles or components thereof) may be reduced from $15.08 using conventional printing methods to $9.00, using the methods herein, assuming all other factors are held constant.

Using the printing methods herein which provide for weighted probability printing, instructions for printing certain images in desired distributions may be provided to the printing apparatus, as described herein, including having each image being loaded to the printing system and assigned a unique number corresponding to that image, a random distribution of those numbers according to the desired probability being prepared, and the printing system being instructed to print the image corresponding to the unique number in the order and in the distribution generated.

ADDITIONAL EXAMPLES

A. A method for printing graphics on an absorbent article component, comprising the steps of:
providing one or more printheads;
providing a substrate extending in a machine direction, the substrate comprising a first surface and an opposing second surface and defining a width in a cross direction;
advancing the substrate in the machine direction past the one or more printheads;
ejecting one or more inks from the one or more printheads onto the first surface of the substrate to define a graphic of a plurality of images, each of the plurality of images not being identical to another;
wherein the distribution of each of the plurality of images printed on the substrate are not all equal to each other.
B. The method of paragraph A, including a step of providing instructions to the one or more printheads to print each of the plurality of images in a particular probability, the sum of the probabilities equaling 100%.
C. The method of paragraph B, wherein the instructions are provided via a controller, the controller being in communication with the one or more printheads.
D. The method of any one of the preceding paragraphs, including a step of assigning a unique identifier corresponding to each of the plurality of image, and loading each of the plurality of images to a printing system carrying out two or more steps of the method; wherein the image corresponding to a given identifier is printed after the identifier is presented to the one or more printheads.
E. The method of paragraph D, including a step of loading each of the plurality of images to the printing system.
F. The method of paragraph D, including a step of preparing a list of the unique identifiers and a random distribution of those identifiers, according to a desired probability for each image to be printed.
G. The method of paragraph F, including a step of instructing the printing system to print the image corresponding to the unique identifier in the distribution generated.
H. The method of any one of the preceding paragraphs, wherein at least one of the one or more inks is an energy curable ink.
I. The method of any one of the preceding paragraphs, wherein at least one of the one or more inks is a water-based ink.
J. The method of any one of the preceding paragraphs, wherein at least one of the one or more inks is a solvent-based ink.
K. The method of any one of the preceding paragraphs, including a step of curing at least one of one or more inks.
L. The method of paragraph K, wherein the step of curing further comprises advancing the printed area past an ink curing apparatus selected from the group of consisting of: an ultra violet light source and an electron beam generator.
M. The method of any one of the preceding paragraphs, wherein the printed image comprises an active graphic.
N. The method of any one of the preceding paragraphs, including a step of converting the substrate into components of disposable absorbent articles.
O. The method of any one of the preceding paragraphs, wherein the absorbent article component is selected from the group consisting of a first waist region of a chassis, a second waist region of a chassis, a crotch region of a chassis, a topsheet, a backsheet, an absorbent core, a leg cuff, a fastening member, a side panels, a connection zone, and a belt.
P. The method of any one of the preceding paragraphs, wherein the absorbent article is selected from the group consisting of diapers, infant training pants, adult incontinence products, and feminine hygiene sanitary pads and pantiliners.
Q. The method of paragraph P, wherein the absorbent article comprises about 98% or more, of particulate absorbent polymer material.
R. The method of paragraph P, wherein the absorbent article comprises about 1% or less, of cellulose fibers.
S. The method of any one of the preceding paragraphs, wherein the substrate comprises a non-woven, a film, or a laminate of non-woven and film.
T. The method of any one of the preceding paragraphs, wherein at least one of the inks comprise an ink and an adhesive.
U. The method of paragraph T, wherein the ink and adhesive combination has a different color than the color of the substrate, and the absorbent article component is selected from a topsheet, a backsheet, and an acquisition layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for the weighted probability printing of graphics on an absorbent article component, comprising the steps of:
   Providing a printing system comprising one or more printheads;
   providing a substrate extending in a machine direction, the substrate comprising a first surface, an opposing second surface, and a plurality of component sections along its length each of which being transformable into a component on an individual absorbent article;
   advancing the substrate in the machine direction past the one or more printheads;
   ejecting one or more inks from the one or more printheads onto the first surface of the substrate to define a graphic of a plurality of images, each of the plurality of images not being identical to another;
   wherein each image is loaded to the printing system and assigned a unique number corresponding to that image, said numbers being listed in a random order and distribution according to a desired probability of being printed;
   wherein instructions are provided to the one or more printheads to print each of the plurality of images in said particular probability, the sum of the probabilities equaling 100%;
   wherein the distribution of each of the plurality of images printed on the substrate are not all equal to each other on a per component section basis.

2. The method of claim 1, wherein the instructions are provided via a controller, the controller being in communication with the one or more printheads.

3. The method of claim 1, including a step of assigning a unique identifier corresponding to each of the plurality of image, and loading each of the plurality of images to a printing system carrying out two or more steps of the method; wherein the image corresponding to a given identifier is printed after the identifier is presented to the one or more printheads.

4. The method of claim 3, including a step of loading each of the plurality of images to the printing system.

5. The method of claim 3, including a step of preparing a list of the unique identifiers and a random distribution of those identifiers, according to a desired probability for each image to be printed.

6. The method of claim 5, including a step of instructing the printing system to print the image corresponding to the unique identifier in the distribution generated.

7. The method of claim 1, wherein at least one of the one or more inks is an energy curable ink.

8. The method of claim 1, wherein at least one of the one or more inks is a water-based ink.

9. The method of claim 1, wherein at least one of the one or more inks is a solvent-based ink.

10. The method of claim 1, including a step of curing at least one of one or more inks.

11. The method of claim 10, wherein the step of curing further comprises advancing the printed area past an ink curing apparatus selected from the group of consisting of: an ultra violet light source and an electron beam generator.

12. The method of claim 1, wherein the printed image comprises an active graphic.

13. The method of claim 1, including a step of converting the substrate into components of disposable absorbent articles.

14. The method of claim 1, wherein the absorbent article component is selected from the group consisting of a first waist region of a chassis, a second waist region of a chassis, a crotch region of a chassis, a topsheet, a backsheet, an absorbent core, a leg cuff, a fastening member, a side panels, a connection zone, and a belt.

15. The method of claim 1, wherein the absorbent article is selected from the group consisting of diapers, infant training pants, adult incontinence products, and feminine hygiene sanitary pads and pantiliners.

16. The method of claim 1, wherein the substrate comprises a non-woven, a film, or a laminate of non-woven and film.

17. The method of claim 1, wherein at least one of the inks comprise an ink and an adhesive.

18. The method of claim 17, wherein the ink and adhesive combination has a different color than the color of the substrate, and the absorbent article component is selected from a topsheet, a backsheet, and an acquisition layer.

19. A method according to claim 1,
   wherein a probability that a particular image of the plurality of images exists at one of the plurality of component sections along the length of the substrate is from 5% to 31%.

20. A method according to claim 1 comprising:
   ejecting one or more inks from the one or more printheads onto the first surface of the substrate to define a graphic of a plurality of images comprising a first absorbent article image comprising a first volume of ink and configured for use on a first individual absorbent article, a second absorbent article image comprising a second volume of ink and configured for use on a second individual absorbent article, a third absorbent article image comprising a third volume of ink and configured for a third individual absorbent article, and a fourth absorbent article image comprising a fourth volume of ink and configured for a fourth individual absorbent article;
   wherein each of the plurality of images not being identical to another;
   wherein the first volume of ink, the second volume of ink, the third volume of ink, and the fourth volume of ink are different from one another;
   wherein multiple sections of the substrate are printed with each of the first absorbent article image, the second absorbent article image, the third absorbent article image, and the fourth absorbent article image; and
   wherein the distribution of each of the plurality of images printed on the substrate are not all equal to each other.

* * * * *